United States Patent [19]

Manring

[11] Patent Number: 4,916,718
[45] Date of Patent: Apr. 10, 1990

[54] PRECISION SCAN POSITION RESOLVER FOR CT SCANNERS

[75] Inventor: John M. Manring, Cleveland Hts., Ohio

[73] Assignee: Picker International, Inc., Highland Hts., Ohio

[21] Appl. No.: 275,783

[22] Filed: Nov. 23, 1988

[51] Int. Cl.$^4$ .............................................. H05G 1/60
[52] U.S. Cl. ........................................... 378/4; 378/15
[58] Field of Search ..................................... 378/4, 15

[56] References Cited

U.S. PATENT DOCUMENTS 4,015,129  3/1977  Manring ............................. 250/360

OTHER PUBLICATIONS

"Synchro and Resolver Conversion" edited by G. Boyes, Chapter 1, pp. 1-32, 1980.

"Magnetic Pickups (Transducers)", General Catalog 0200, pp. 3-4.

Primary Examiner—Craig E. Church
Attorney, Agent, or Firm—Fay, Sharpe, Beall, Fagan, Minnich & McKee

[57] ABSTRACT

A scan frame (12) is mounted to a stationary frame (10) for rotation about a scan circle (14). A two speed resolver (20) has one circular core (36) mounted to the gantry and another circular core (32) mounted to the stationary frame. A primary winding (30a, 30b) on one of the cores receives AC excitation power from an excitation generator (58). Quadrature coarse resolution windings (54, 56) and quadrature fine resolution windings (50, 52) both in quadrature produce output signals indicative of the relative angle of the scan frame to the stationary frame. An angular position digitizing circuit (60) converts the analog sine/cosine signals into a digital angle signal.

16 Claims, 3 Drawing Sheets

PRECISION SCAN POSITION RESOLVER FOR CT SCANNERS

BACKGROUND OF THE INVENTION

The present invention relates to the art of medical diagnostic imaging. It finds particular application in conjunction with CT scanners and will be described with particular reference thereto. However, it is to be appreciated that the invention might also find application in conjunction with other diagnostic devices in which equipment is rotated peripherally around an examination region.

In CT scanners, a fan shaped beam of radiation is rotated around a portion of a patient disposed in a region of interest or scan circle. Radiation detectors disposed across the scan circle receive rays of radiation that have traversed the scan circle and the patient. The detectors are periodically sampled to measure the intensity of radiation impinging thereon. Concurrently with each radiation intensity sampling, the position of the x-ray source is monitored. The positions of the x-ray source and the sampled detector describe the path or ray of radiation with which the intensity reading is attributed. Various image reconstruction algorithms may be implemented to reconstruct an image representation from the intensity samplings and the x-ray source position readings. Thus, the accuracy with which the position of the x-ray source is determined affects the accuracy and resolution of the resultant image.

Various hardware has been developed for measuring the angular position of a rotating gantry on which the x-ray source is mounted. In one technique, a belt was driven by gantry rotation to drive an incremental position encoder. In another technique, the incremental encoder was driven by a direct gear drive rather than a belt drive. The position encoder produced an output stream of pulses whose frequency was indicative of the speed of rotation of the gantry. That is, a pulse was generated each time the gantry rotated a preselected increment of arc.

A typical incremental position encoder included a light beam detected by an photodiode or other optical detector. The belt drive rotated a slotted wheel which broke and passed the light beam as the gantry rotated. Magnetic incremental encoders have also been used to indicate rotation. Hall effect sensors have been used to monitor breaking and passing of magnetic flux lines such as with a slotted ferrous wheel or moving magnetic sources. Magnetic pickups have been used as ferrous material proximity detectors to produce electrical pulses in response to passing ferrous teeth or vanes. To determine the direction of rotation, two analogous encoders provided a pair of pulse trains with a preselected phase relationship other than 0° or 180°, e.g. a 90° or quadrature relationship. Direction of rotation was indicated by which pulse train was leading and which was trailing.

One of the problems with belt drives is that the belts tend to stretch, adversely affecting the accuracy of the encoder output. Also, there tends to be play or slippage of the belt relative to the drive and driven gears. In a direct gear drive, there is play between the gears to keep them from binding. As the gears wear, the play becomes greater.

One solution for eliminating the play of belt and gear drives is described in U.S. Pat. No. 4,015,129. A hollow glass timing disc etched with a periodic grating circumscribed the scan circle. An optical sensor, such as a light source and photodetector was mounted on the gantry to shine light through the periodic grating marks on the timing disc. In this manner, rotation of the optical sensor relative to the timing disc caused a series of pulses, each pulse occurring after a preselected angular increment of rotation. In order to reduce positional reading errors attributable to mechanical play, a Teflon rider was provided between the ring and the optical sensor. One of the problems with the hollow glass incremental encoder is that it was very sensitive to scratches and manufacturing blemishes.

The prior art mechanically driven incremental sensors had an inherent inaccuracy due to mechanical play. Moreover, the incremental encoders only provided indications of incremental movement. Additional circuitry was required to establish an initial reference or starting point for the scanner and to determine the current position from the pulse trains.

The present invention provides a new and improved position encoder which overcomes the above referenced problems and others.

SUMMARY OF THE INVENTION

In accordance with one aspect of the present invention, a CT scanner assembly is provided. The scanner includes a housing which has a stationary portion circumscribing a scan circle. An x-ray tube is mounted on a rotating gantry which rotates about the scan circle. A position resolver includes a primary winding and quadrature secondary windings such that the secondary windings produce two output signals that have a sine/cosine relationship. One of the primary windings is disposed circumscribing the scan circle on one of the stationary housing and rotating gantry and the second winding is mounted on the other. The primary and secondary windings are mounted in close proximity to provide an electromagnetic coupling therebetween. An image reconstruction means reconstructs image representations from indications of an angular position of the x-ray tube about the scan circle and the outputs of radiation detectors that receive radiation from the x-ray tube.

In accordance with another more limited aspect of the present invention, the primary winding is mounted to the gantry for rotation therewith and the secondary windings are mounted to the stationary housing. Means are provided for conveying an excitation current to the primary winding from an excitation current supply off the gantry. In one embodiment, slip rings are provided for communicating the excitation current to gantry mounted secondary windings. In another embodiment, a brushless resolver is provided in which an axial transformer assembly transfers the excitation current.

In accordance with another aspect of the present invention, a medical diagnostic scanner is provided. An x-ray source is mounted for rotation about a scan circle. First and second circular ferromagnetic resolver cores are disposed circumferentially around the scan circle. One is mounted for rotation with the x-ray source and the other is stationarily mounted. Radiation detectors detect radiation from the x-ray source that has traversed the scan circle. The primary winding assembly is magnetically connected with one of the cores and a secondary winding assembly with the other. A power supply supplies AC excitation power to the primary winding and a converter converts the output of the secondary winding to an indication of a relative angular position of the first and second resolver cores.

In accordance with another aspect of the present invention, a CT scanner is provided. A gantry rotates an x-ray tube about a scan circle. A two speed resolver, which surrounds the scan circle, is mounted in part to the rotating gantry and in part to a stationary frame. The output signals of the two speed resolver are indicative of rotation and relative angular position of the gantry and the stationary frame.

One advantage of the present invention is that it provides an indication of the angular position of the gantry, rather than merely an indication of angular rotation.

Another advantage of the present invention resides in its accuracy. The attendant errors of mechanical gearing and drive belts are eliminated.

Another advantage of the present invention is that it is space efficient.

Still further advantages of the present invention will become apparent upon reading and understanding the following detailed description.

BRIEF DESCRIPTION OF THE DRAWINGS

The invention may take form in various parts and arrangements of parts. The drawings are only for purposes of illustrating a preferred embodiment and are not to be construed as limiting the invention.

DETAILED DESCRIPTION OF THE PREFERRED EMBODIMENTS

Figure 1:
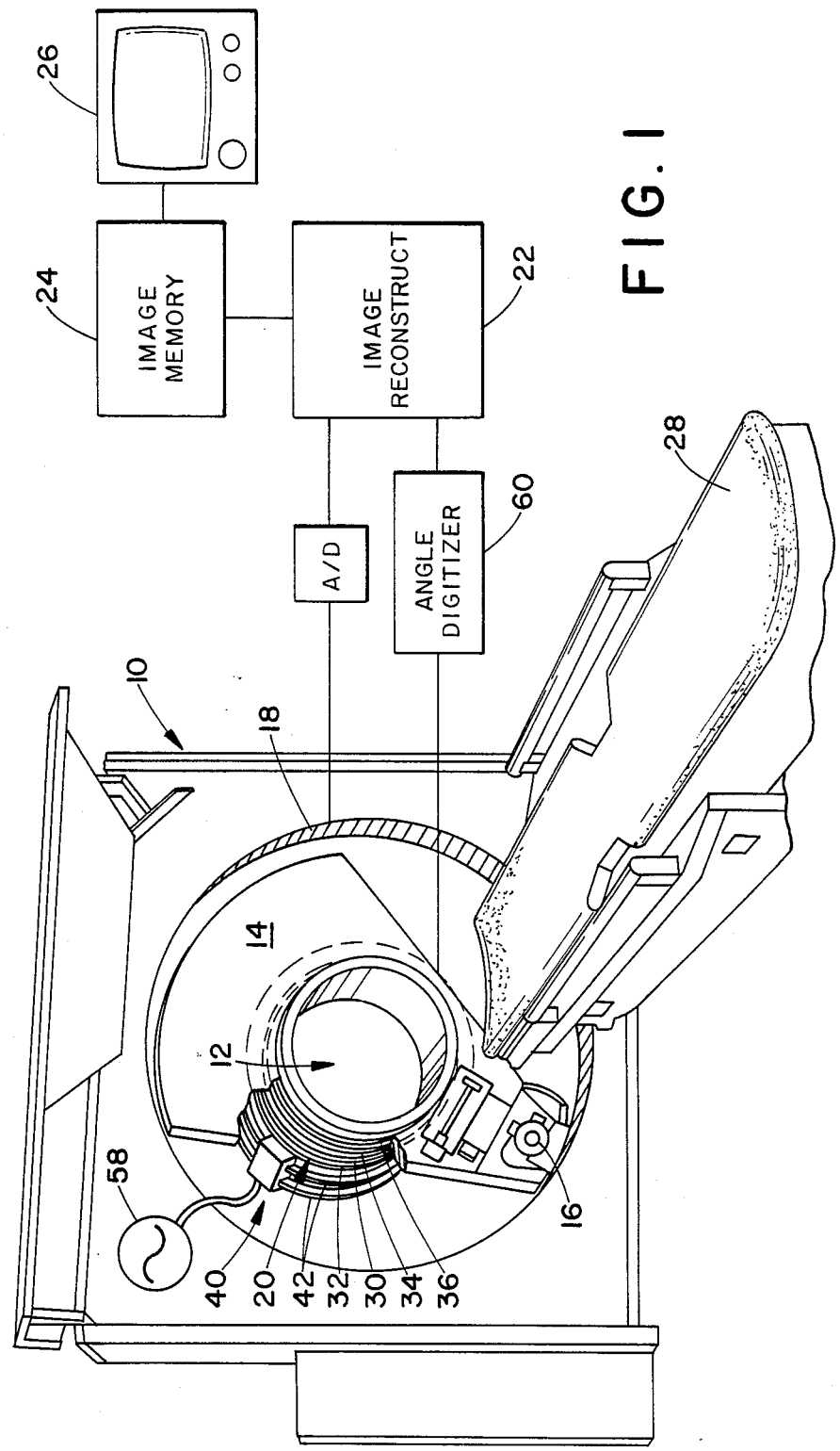
FIG. 1 is a diagrammatic illustration of a CT scanner in accordance with the present invention.

A CT scanner includes a stationary gantry 10. A central opening or scan circle 12 is defined through the housing. A scan frame 14 is mounted for rotation about the scan circle 12. An x-ray tube 16 (mounted on the scan frame 14) projects a fan shaped beam of radiation through the scan circle or examination region 12. Detectors 18 convert the radiation that has traversed the scan circle into electrical signals linearly proportional to the intensity of received radiation.

A large hollow, two speed resolver 20 provides output signals indicative of the relative angular position of the scan frame 14 or x-ray source and the stationary gantry 10. An image reconstruction means 22 reconstructs an image representation from radiation attenuation or intensity signals received by the detectors and the angular position as monitored by the resolver at which each x-ray reading was sampled. The reconstructed image representation is stored in an image memory 24 for display on a video monitor 26. Optionally, one or more image representations may be subject to further processing, stored on tape or disk, or the like. A patient couch 28 selectively advances portions of a patient or other object to be imaged into the examination region 12.

Figure 3:
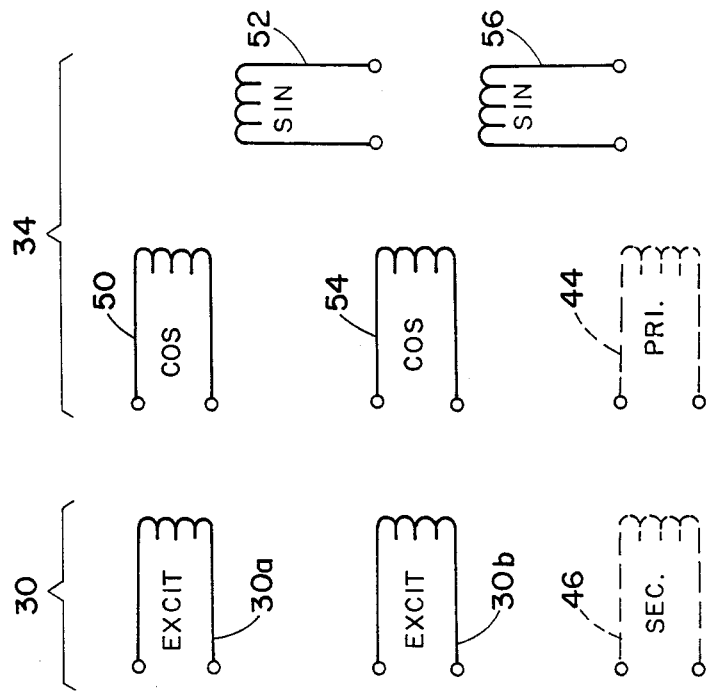
FIG. 3 is a diagrammatic illustration of resolver windings.
Figure 2:
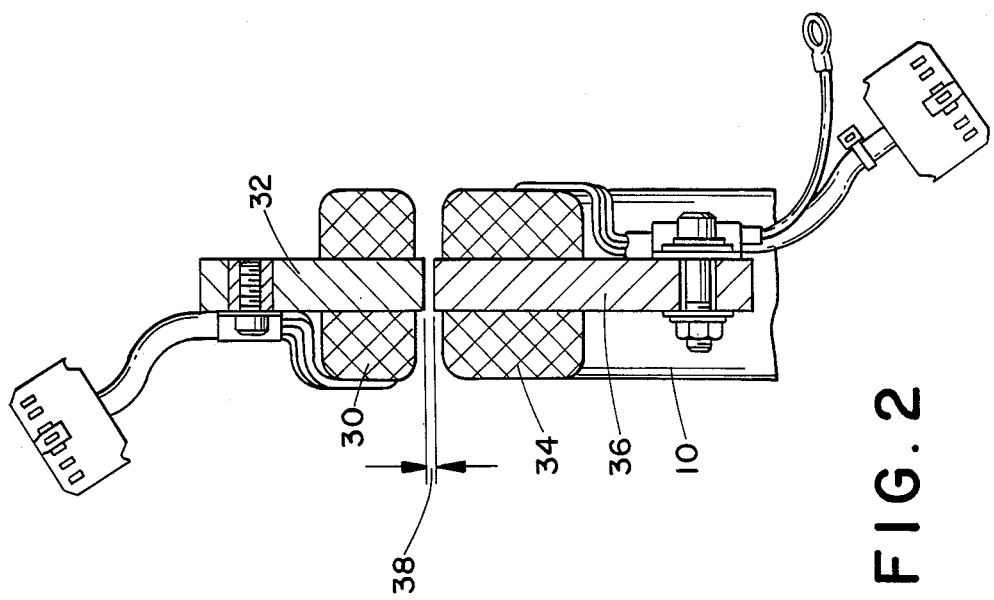
FIG. 2 is a sectional view taken transversely through the resolver of FIG. 1.

With reference to FIGS. 2 and 3, the resolver includes a primary or excitation winding 30 arranged on a circular ferrous core 32 that circumscribes the examination region. Secondary or output windings 34 are wound in quadrature on a circular ferrous core 36 that also extends circumferentially around the examination region 12 One of the winding cores is mounted to the stationary housing and the other is mounted to the rotor for rotation therewith. The resolver cores are mounted in sufficiently close physical proximity, with only a narrow gap 38 therebetween, that a magnetic coupling is created.

A power supply 40 supplies an AC excitation current $A\sin\omega t$ to the primary winding. In the illustrated embodiment, slip rings 42 are provided for conveying the electrical power to the primary winding which is mounted to the gantry. Optionally, other power transfer devices, such as an axial core transformer, may communicate the electrical power to the primary winding. The axial core transformer may include a pair of concentric circular cores, one with a primary and the other with a secondary winding. In a preferred axial core transformer, a primary transformer winding 44 is added around the stator core 36 and a secondary transformer winding 46 is added around the rotor core 32.

The output or secondary winding 34 in the illustrated embodiment is stationarily mounted on the housing. The output winding includes at least four coils or windings. First, a pair of fine or high resolution windings 50, 52 are wound on the secondary winding core. The two windings have a quadrature relationship. That is, one of the windings produces an output signal $B\sin\omega t\sin\theta$ whose amplitude and phase varies in proportion to the sine of the relative angular position $\theta$ of the stationary gantry and the rotating scan frame and the other winding provides an output signal $B\sin\omega t\cos\theta$ that varies with the cosine of this angle $\theta$. The zero relative angle between the two may be arbitrarily selected. However, once the primary and secondary windings are mounted, the arbitrary selected zero angle is fixed. In the preferred embodiment, the primary fine resolution input winding 30a and the high or fine resolution windings provide 150 cycles per revolution of the gantry.

As yet another embodiment, the two fine resolution windings 50, 52 may have other than a quadrature or 90° relationship. For example, one could indicate sine or cosine and the other could be a coarse resolution winding which provides about 4 cycles per revolution to indicate only the quadrant. As yet another embodiment, the two windings may have an angular relationship other than 90°. Because a relationship other than a 90° relationship is not a sine/cosine relationship, more complex mathematics may be required to resolve the relative angular position of the gantry on the stationary frame.

In the preferred embodiment, the secondary winding further includes coarse output windings 54, 56 also in quadrature. The coarse primary winding 30b and the course output winding produce one position cycle per revolution to provide an indication of which fine cycle the rotating scan frame is in.

Figure 4:
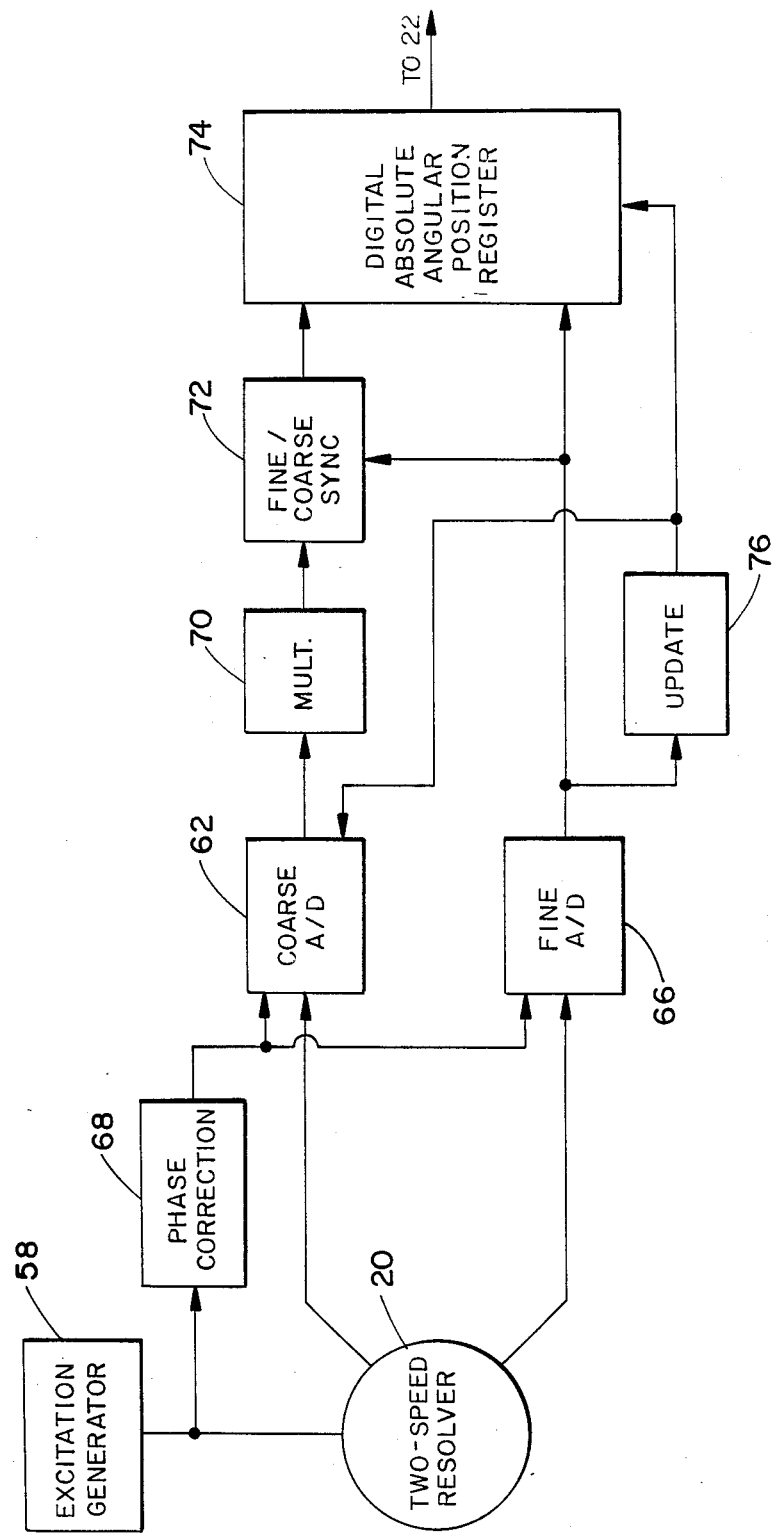
FIG. 4 is a diagram of a circuit for digitizing the analog signals from the resolver.

With reference to FIG. 4, the power supply 40 includes an excitation generator 58 which applies an excitation signal to the primary winding coils 30a and 30b, e.g. a 5 volts rms signal in the range of 2 to 5 kilohertz. A digital angular position circuit 60 converts the analog output of the two speed resolver into digital representations of rotation and relative angular position of the x-ray source 16 and the detectors 18. The coarse resolution sine and cosine output signals of the two speed resolver 20 are conveyed to a coarse analog-to-digital converter 62 which produces a 12 bit digital representation. The fine resolution sine and cosine output signals are digitized by a fine resolution analog-to-digital converter 66 to a 12 bit representation. A phase correction means 68 provides a correction based on the excitation signal.

If the coarse and fine resolution windings are in a ratio that is an even binary relationship, then the coarse and fine resolution digital signals can be merely combined or added. However, if the ratios are not an even binary number, such as the 150:1 ratio of the preferred embodiment, a multiplier means 70 multiplies the coarse digital signal to bring it into binary equivalence with the fine digital signal. A coarse/fine sync 72 circuit combines the fine and coarse digital signals. In the preferred embodiment, the eight most significant bits are ascertained. A position register 74 is addressed by the digital signals, specifically the eight most significant bits from the sync circuit 72 and the eight most significant bits of the fine resolution signal, and produces a 16 bit output signal indicative of angular position. In the preferred embodiment, the angular and digital position is accurate to about one part to 54,000, i.e. less than ±24 arc seconds. An update circuit 66 indexes the coarse resolution analog-to-digital converter 56 and the angular position register 74 after each sampling of the fine resolution analog-to-digital converter 66.

The invention has been described with reference to the preferred embodiment. Clearly, modifications and alterations will occur to others upon reading and understanding the preceding detailed description of the preferred embodiment. It is intended that the invention be construed as including all such alterations and modifications insofar as they come within the scope of the appended claims or the equivalents thereof.

Having thus described the preferred embodiments, the invention is now claimed to be:

1. A CT scanner comprising:
   a stationary frame having an aperture therein within which a scan circle is defined;
   a rotating scan frame assembly for rotating an x-ray source around the scan circle;
   a plurality of radiation detectors for detecting radiation from the x-ray source that has passed through the scan circle;
   a resolver including magnetically coupled, concentric primary and secondary windings, the primary and secondary windings being along a circular path that is larger in diameter than the scan circle, one of the primary and secondary windings being mounted to the stationary frame circumscribing the scan circle and the other being mounted to the rotating scan frame for rotation therewith; and,
   an image reconstruction means for reconstructing an image representation, the image reconstruction means being interconnected with the radiation detectors for receiving radiation intensity signals therefrom and being connected with the resolver for receiving output signals therefrom indicative of a relative angular position of the x-ray source and the stationary frame at each sampling of the radiation detectors.

2. The scanner as set forth in claim 1 wherein the secondary winding is a pair of windings which produces two output signals that have a sine/cosine relationship.

3. The scanner as set forth in claim 1 wherein the resolver is a two speed resolver in which the secondary coil includes low pitch windings to provide a coarse indication of angular rotation and fine resolution windings of a higher pitch to provide a more precise indication of angular position.

4. The scanner as set forth in claim 3 further including an analog-to-digital converter means for converting outputs of the coarse and fine windings to digital signals.

5. The scanner as set forth in claim 4 further including a combining means for combining the coarse and fine digital signals.

6. The scanner as set forth in claim 4 further including a position register which is addressed by the combined coarse and fine digital signals to retrieve an angle that is indicative of a relative angular position of the gantry and frame.

7. The scanner as set forth in claim 3 wherein at least the fine resolution winding is a quadrature winding which produces two output signals having a sine and cosine relationship.

8. The scanner as set forth in claim 7 further including analog-to-digital converter means for converting outputs of the coarse and fine resolution windings to digital signals.

9. The scanner as set forth in claim 8 further including a combining means for combining the coarse and fine digital signals.

10. The scanner as set forth in claim 9 further including a position register which is addressed by the combined coarse and fine digital signals to produce an indication of angular position of the gantry relative to a preselected reference orientation.

11. The apparatus as set forth in claim 1 wherein the primary winding is mounted to the rotating scan frame and the secondary winding is connected to the stationary frame and further including means for transferring AC power from an AC power supply mounted on the stationary frame to the primary winding on the rotating scan frame.

12. The scanner as set forth in claim 11 wherein the power transfer means includes an axial transformer means with a primary coil mounted to the stationary frame and a secondary coil mounted to the rotating scan frame.

13. The scanner as set forth in claim 11 wherein the power transfer means includes a slip ring.

14. A medical diagnostic scanner comprising:
    an x-ray source mounted for rotation about a scan circle;
    a first circular, ferromagnetic resolver core disposed circumferentially around the scan circle and operatively connected with the x-ray source for rotation therewith;
    a second circular, ferromagnetic resolver core mounted stationarily around the scan circle in a magnetically coupled relationship with the rotating resolver core;
    radiation detectors for detecting radiation from the x-ray source that has traversed the scan circle;
    a primary winding assembly magnetically connected with one of the cores and a secondary winding assembly connected with the other;
    a power supply for supplying AC power to the primary winding; and,
    a converter for converting an output of the secondary winding to an indication of a relative angular position of the first and second resolver cores.

15. A CT scanner comprising:

a scan frame for rotating an x-ray tube about a scan circle, the scan frame being rotatably mounted relative to a stationary frame; and, a two speed resolver surrounding the scan circle, the two speed resolver being mounted in part to the stationary frame and in part to the scan frame for producing output signals indicative of a rotation and relative angular position of the scan frame and the stationary frame.

16. The CT scanner as set forth in claim 15 wherein the two speed resolver includes a fine resolution secondary winding that produces a fine resolution output signal indicative of the angular position of the scan frame and a coarse resolution secondary winding that produces only one position cycle for each scan frame revolution.

* * * * *